(12) United States Patent
Saw et al.

(10) Patent No.: US 11,395,686 B2
(45) Date of Patent: Jul. 26, 2022

(54) BONE FIXATION PLATE AND METHOD OF USING THEREOF

(71) Applicants: Khay-Yong Saw, Kuala Lumpur (MY); Reza-Ching-Soong Ng, Kuala Lumpur (MY); Caroline-Siew-Yoke Jee, Kuala Lumpur (MY)

(72) Inventors: Khay-Yong Saw, Kuala Lumpur (MY); Reza-Ching-Soong Ng, Kuala Lumpur (MY); Caroline-Siew-Yoke Jee, Kuala Lumpur (MY)

(73) Assignees: Khay-Yong Saw, Kuala Lumpur (MY); Reza-Ching-Soong Ng, Kuala Lumpur (MY); Caroline-Siew-Yoke Jee, Kaula Lumpur (MY)

( * ) Notice: Subject to any disclaimer, the term of this patent is extended or adjusted under 35 U.S.C. 154(b) by 9 days.

(21) Appl. No.: 16/853,452

(22) Filed: Apr. 20, 2020

(65) Prior Publication Data

US 2021/0322073 A1    Oct. 21, 2021

(51) Int. Cl.
*A61B 17/80* (2006.01)
*A61B 17/68* (2006.01)
(Continued)

(52) U.S. Cl.
CPC ...... *A61B 17/8061* (2013.01); *A61B 17/1662* (2013.01); *A61B 17/8052* (2013.01);
(Continued)

(58) Field of Classification Search
CPC ............ A61B 17/8061; A61B 17/1662; A61B 17/8052; A61B 17/8057; A61B 17/7059;
(Continued)

(56) References Cited

U.S. PATENT DOCUMENTS 5,304,180 A    4/1994   Slocum
6,302,887 B1   10/2001  Spranza et al.
(Continued)

FOREIGN PATENT DOCUMENTS

CN    209847351 U    12/2019
EP    2 756 814 B1   3/2018
(Continued)

OTHER PUBLICATIONS

Cao Ba Huong, University of Medicine and Pharmacy, Ho Cho Minh city, slides of screw and plates fixation, available at https://www.slideshare.net/BaHuong/screws-and-plates-fixation, published Mar. 30, 2015, 38 pages provided.
(Continued)

*Primary Examiner* — Marcela I. Shirsat
(74) *Attorney, Agent, or Firm* — Hamre, Schumann, Mueller & Larson, P. C.

(57) ABSTRACT

The disclosure provides a fixation device for internal fixation of an osteotomy below the tibial tuberosity. The fixation plate including a top-end portion including three pinholes, three screw holes, and a first Combi hole; a bottom-end portion including a second Combi hole, two screw holes, and one pinhole; and a connection portion connecting the top-end portion to the bottom-end portion. The top-end portion is capable of fixating the portion of the tibia above a cut of the osteotomy, and the bottom-end portion is capable of fixating the portion of the tibia below the cut.

19 Claims, 11 Drawing Sheets

(51) Int. Cl.
*A61B 17/70* (2006.01)
*A61B 17/16* (2006.01)

(52) U.S. Cl.
CPC ...... *A61B 17/8057* (2013.01); *A61B 17/7059* (2013.01); *A61B 2017/681* (2013.01)

(58) Field of Classification Search
CPC ... A61B 17/80; A61B 17/8085; A61B 17/809; A61B 17/8095; A61B 17/8065; A61B 17/1728; A61B 17/808; A61B 2017/681
USPC ................ 606/291, 280, 283, 284, 286, 902
See application file for complete search history.

(56) References Cited

U.S. PATENT DOCUMENTS

| | | | |
|---|---|---|---|
| 6,623,486 | B1 * | 9/2003 | Weaver ................ A61B 17/80 606/281 |
| 7,282,053 | B2 | 10/2007 | Orbay |
| 7,722,653 | B2 | 5/2010 | Young et al. |
| 8,133,230 | B2 | 3/2012 | Stevens et al. |
| 8,197,521 | B2 | 6/2012 | Sixto, Jr. et al. |
| 8,246,661 | B2 | 8/2012 | Beutter et al. |
| 8,523,921 | B2 | 9/2013 | Horan et al. |
| 8,821,580 | B2 | 9/2014 | DaSilva |
| 8,828,087 | B2 | 9/2014 | Stone et al. |
| 9,320,553 | B2 | 4/2016 | Katrana et al. |
| 10,226,288 | B2 | 3/2019 | Sidebotham et al. |
| 10,299,841 | B2 | 5/2019 | Dunlop et al. |
| 2003/0135212 | A1 | 7/2003 | Y. Chow |
| 2006/0264949 | A1 * | 11/2006 | Kohut ................ A61B 17/8061 606/71 |
| 2009/0024172 | A1 | 1/2009 | Pizzicara |
| 2009/0318921 | A1 | 12/2009 | White et al. |
| 2012/0265255 | A1 * | 10/2012 | Hilse ................ A61B 17/8057 606/290 |
| 2013/0211463 | A1 | 8/2013 | Mizuno et al. |
| 2013/0238032 | A1 * | 9/2013 | Schilter ................ A61B 17/80 606/281 |
| 2016/0128745 | A1 * | 5/2016 | Sidebotham ........ A61B 17/8095 606/281 |
| 2016/0143663 | A1 | 5/2016 | Schemitsch et al. |
| 2017/0007304 | A1 | 1/2017 | Kuroda et al. |
| 2017/0027627 | A1 | 2/2017 | Paik |
| 2018/0325568 | A1 | 11/2018 | Wotton |
| 2019/0090921 | A1 | 3/2019 | Kuroda et al. |

FOREIGN PATENT DOCUMENTS

| | | |
|---|---|---|
| KR | 10-2016-0145864 A | 12/2016 |
| WO | 2015/171200 A1 | 11/2015 |

OTHER PUBLICATIONS

"TOMOFIX® Osteotomy System", surgical technical guide, available at www.depuysynthes.com at least as early as 2017; 41 pages provided.
International Search Report issued in International Application No. PCT/MY2021/050027, dated Aug. 27, 2021, 6 pages.
Written Opinion issued in International Application No. PCT/MY2021/050027, dated Aug. 27, 2021, 5 pages.

* cited by examiner

BONE FIXATION PLATE AND METHOD OF USING THEREOF

FIELD

The disclosure relates to the internal fixation of a bone in an osteotomy. Specifically, the disclosure relates to a fixation plate for a tibial osteotomy below the tibial tuberosity.

BACKGROUND

The osteotomy is a surgical operation on the bone and is usually performed to fix abnormalities or conditions in different bones and joints, for example, knee, hip, elbow, spine, big toe, etc. Examples of the abnormalities or conditions can include but are not limited to, for example, hallux valgus, coxa vara, genu valgum, and genu varum. The osteotomy can be performed to repair a damaged joint, realign a deformed bone, relieve arthritis pain, straighten a bone healed crookedly following a fracture, etc.

A conventional tibial osteotomy of the knee involves making a cut at the tibia above its tibial tuberosity and is referred to as a high tibial osteotomy (HTO). There are numerous types of HTO, and the most commonly performed techniques of HTO are opening or closing wedge osteotomy. Once the calculation of the correction degree has been made, the osteotomy can be performed using an oscillating saw or osteotome. For open wedge osteotomy, an internal fixation plate is then fixed over the opening wedge once the desired degree of correction is achieved. A bone graft (synthetic or natural) may optionally be inserted at the open wedge to enhance bone growth and provide further stability.

SUMMARY

Embodiments herein provide a fixation plate for internal fixation of an osteotomy below the tuberosity of a tibia. The fixation plate includes an elongated body having a top end and a bottom end opposing the top end along a length direction of the fixation plate. The elongated body, viewed from the top end to the bottom end, includes a top-end portion, a connection portion, and a bottom-end portion.

In an embodiment, the top-end portion includes pinholes, screw holes, and one or more Combi holes. A Combi hole is a combination of two or more overlapping holes. In an embodiment, the top-end portion includes three pinholes, three screw holes, and a first Combi hole. Each of the pinholes of the top-end portion is dispersed between two of the three screw holes of the top-end portion. In an embodiment, the three pinholes and the three screw holes are arranged alternately. The three screw holes are arranged in an inverted triangle configuration with two of the pinholes above the third. The first Combi hole is disposed below the three pinholes and the three screw holes of the top-end portion.

In an embodiment, the pinholes of the top-end portion are disposed outside of a triangle formed by connecting the centers of the screw holes of the top-end portion. In an embodiment, the pinholes are arranged in a non-inverted triangle. In an embodiment, each pinhole is non-collinear between two of the three screw holes.

The connection portion connects the top-end portion to the bottom-end portion. In an embodiment, the connection portion is not provided with a through-hole.

The bottom-end portion can include one or more Combi holes, two or more screw holes, and one or more pinholes. In an embodiment, the bottom-end portion includes a second Combi hole, two screw holes, and one pinhole. The second Combi hole is disposed above the two screw holes and the pinhole, view from the top end to the bottom end.

In an embodiment, the pinhole of the bottom-end portion is disposed between the two screw holes of the bottom-end portion.

In an embodiment, at least one of the two screw holes of the bottom-end portion is a conical screw hole.

In an embodiment, one of the two screw holes of the bottom-end portion is closer to the distal end of the bottom-end portion than the other and is a double lead conical thread hole having a pitch of at or about 0.5 mm, a wall thickness of at or about 0.425 mm, a cone degree of at or about $20.0°±0.2°$, and at or about $60.0°±0.2$ relative to the center of the bottom-end.

In an embodiment, centers of the first Combi hole, the second Combi hole, the two screw holes of the bottom-end portion, and the pinhole of the bottom-end portion are in alignment with the mid-width line of the bottom-end portion. In an embodiment, centers of the first Combi hole, the second Combi hole, the two screw holes of the bottom-end portion, and the pinhole of the bottom-end portion are not in alignment.

In an embodiment, each of the first and second Combi holes includes one threaded hole section and one DCP (dynamic compression plate) hole section.

In an embodiment, the first Combi hole is identical to the second Combi hole. In an embodiment, the first and the second Combi holes are oriented in a head to head manner.

In an embodiment, the top-end portion is bendable or twistable or bent or twisted to fit the three-dimensional contour of the portion of the tibia above the osteotomy.

In an embodiment, the fixation plate is at or about $111.5±0.5$ mm long, the top-end portion is at or about $27.5±0.20$ wide, and the bottom-end portion is at or about $17.5±0.20$ wide.

In an embodiment, the bottom-end portion has a strip shape. In an embodiment, the bottom-end portion has a semicircular distal end.

In an embodiment, the first and the second Combi holes each are configured so that screws they receive do not go in or through the osteotomy.

In an embodiment, the tibial osteotomy below the tibial tuberosity includes cutting a tibia at a site below the tibial tuberosity to obtain a cut tibia; and fixating the cut tibia with the fixation plate.

In an embodiment, the tibial osteotomy below the tibial tuberosity further includes realigning the cut tibia.

In an embodiment, cutting a tibia at a site below the tibial tuberosity includes prying the cut of the tibia open to obtain a wedge-shaped opening.

In an embodiment, fixating the cut tibia with a fixation plate includes installing screws into the screw holes of the fixation plate.

In an embodiment, the screws installed in the bottom-end portion $300c$ are generally parallel to each other, and are angled at or about $7.36°$ relative to line Y that is perpendicular to the main plane of the fixation plate. In an embodiment, the screw at the first screw hole of the top-end portion is angled at or about $6.4°$ relative to line Y. In an embodiment, the screw at the first Combi hole is angled at or about $32.45°$ relative to line Y. In an embodiment, the angle between the screw at the first Combi hole and the screw at the third screw hole of the top-end portion is at or about $20.912°$. In an embodiment, the angle between the screw at the first Combi hole and the screw at the first screw hole of the top-end portion is at or about $1.345°$. In an embodiment, the angle between the screw at the Combi hole and the screw at the second screw hole of the top-end portion is at or about 1.802°.

BRIEF DESCRIPTION OF THE DRAWINGS

References are made to the accompanying drawings that form a part of this disclosure, and which illustrate embodiments in which the devices, systems, and methods described in this specification can be practiced.

FIG. 3 B schematically illustrates openings of the hole 324 of FIG. 3 A, according to an embodiment.

FIG. 3 C schematically illustrates the angle of the hole 330 of FIG. 3 A relative to the center of its bottom, in accordance with an embodiment.

FIG. 3 D schematically illustrates the midsection of the hole 330 of FIG. 3 A, in accordance with an embodiment.

FIG. 3 E schematically illustrates an enlarged view of the thread portion A of FIG. 3 D, according to an embodiment.

FIG. 3 F schematically illustrates a cross-section of the fixation plate of FIG. 3 A along line X3, according to an embodiment.

Like reference numbers represent like parts throughout.

DETAILED DESCRIPTION

The disclosure relates to the internal fixation of a bone. Specifically, the disclosure relates to an osteotomy below the tibial tuberosity. More specifically, the disclosure relates to a fixation plate for a tibial osteotomy below the tibial tuberosity and a method of using the fixation plate.

The term "a", "an", or "the" cover both the singular and the plural reference, unless the context clearly dictates otherwise. The terms "comprising", "having", "including", and "containing" are open-ended terms, which means "including but not limited to", unless otherwise indicated.

Certain values herein are preceded by the term "about". The term "about" herein provides literal support for the exact value that it precedes, as well as a range that is near to or approximately the value that the term precedes. In an embodiment, the range is from 70% to 130% of the exact value that the term "about" precedes. In an embodiment, the range is from 80% to 120% of the exact value that the term "about" precedes. In an embodiment, the range is from 90% to 110% of the exact value that the term "about" precedes. In an embodiment, the range is from 99% to 101% of the exact value that the term "about" precedes. For example, if the exact value is 100, the range from 70% to 130% of the exact value is 70 to 130.

A tibial osteotomy is a surgical operation for adjusting or changing the alignment of the tibia to correct abnormalities caused by, for example, birth defects, diseases, arthritis, or the like.

A tibial osteotomy below the tibial tuberosity is a surgical operation that involves cutting a tibia at a site below the tibial tuberosity and then realigning and fixating the cut tibia with a fixation plate.

The disclosure herein provides a fixation plate suitable for the tibial osteotomy below the tibial tuberosity. The fixation plate is suitable for realigning and fixating the two portions of bones at both sides of the cut made below the tibial tuberosity.

The fixation plate herein exhibits advantages over those for the conventional high tibia osteotomy in surgical operation and proper fixation. For example, the fixation plate herein has less chance of causing cancellous bone collapsing and can minimize tibial plateau fracture. The fixation plate herein can also minimize neurovascular bundle injury and disruption of the periosteum and reduces stiffness in the knee after the surgery.

Figure 1:
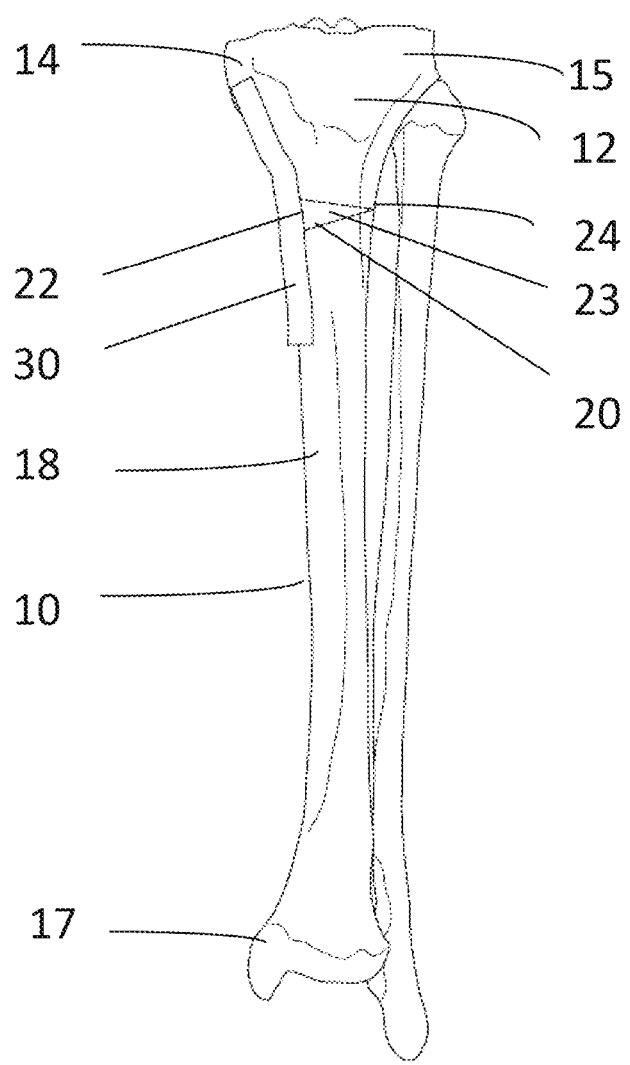
FIG. 1 schematically illustrates a tibial osteotomy below the tibial tuberosity, according to an embodiment.

Referring to FIG. 1, FIG. 1 illustrates an embodiment of the tibial osteotomy below the tibial tuberosity. The tibia 10 includes a tibia tuberosity 12. The tibial tuberosity 12 is a large oblong elevation on the proximal, anterior aspect of the tibia 10, just below where the anterior surfaces of the lateral condyle 14 and the medial condyle 15 end. The tibial osteotomy below the tibial tuberosity can involve cutting the tibia 10, resulting in a cut 20. The cut 20 can include an osteotomy opening 22. In an embodiment, the tibial osteotomy below the tibial tuberosity is an opening wedge osteotomy, which involves "swing" or "cracking" opening the osteotomy opening 22 to form an opening wedge for an angular correction. In an embodiment, the portion of bone 24 opposing the osteotomy opening 22 can function as a hinge and is referred to as osteotomy hinge 24. In an embodiment, the cut 20 can be "swung" opened via the osteotomy hinge 24 to carry out an angular correction.

In an embodiment, the tibial osteotomy below the tibial tuberosity involves a bone grafting. In an embodiment, an implant 23 can be inserted into the cut 20 from the osteotomy opening 22 for carrying out an angular correction. In an embodiment, the implant 23 is an artificial bone or the like. The shape of the implant 23 can be adapted to fit the contour of the cut 20. In an embodiment, the implant is trapezoidal or the like. In an embodiment, the implant is wedge-shaped or the like.

The cut 20 can be made below the tibial tuberosity 12 and above the distal end 17 of the tibia 10. In an embodiment, the cut 20 resides slightly below the tibial tuberosity 12. In an embodiment, the cut 20 is made in the tibial shaft 18. In an embodiment, the cut 20 resides close to the middle of the tibial shaft 18. In an embodiment, the cut 20 is made at a site in the region from the medial side to the lateral side. In an embodiment, the cut 20 resides at the medial side of the tibia 10. In an embodiment, the cut 20 resides at the lateral side of the tibia 10.

In an embodiment, a fixation plate 30 can have an elongated shape, and can be attached to the side of the tibia 10 where the osteotomy opening 20 resides, namely the osteotomy side, for fixating the bone portions at both sides of the osteotomy opening 22. The fixation plate 30 can be attached to the tibia 10 with screws, pins, or the like. In an embodiment, the fixation plate 30 is capable of fitting a patient-specific anatomical surface on the osteotomy side.

Figure 2:
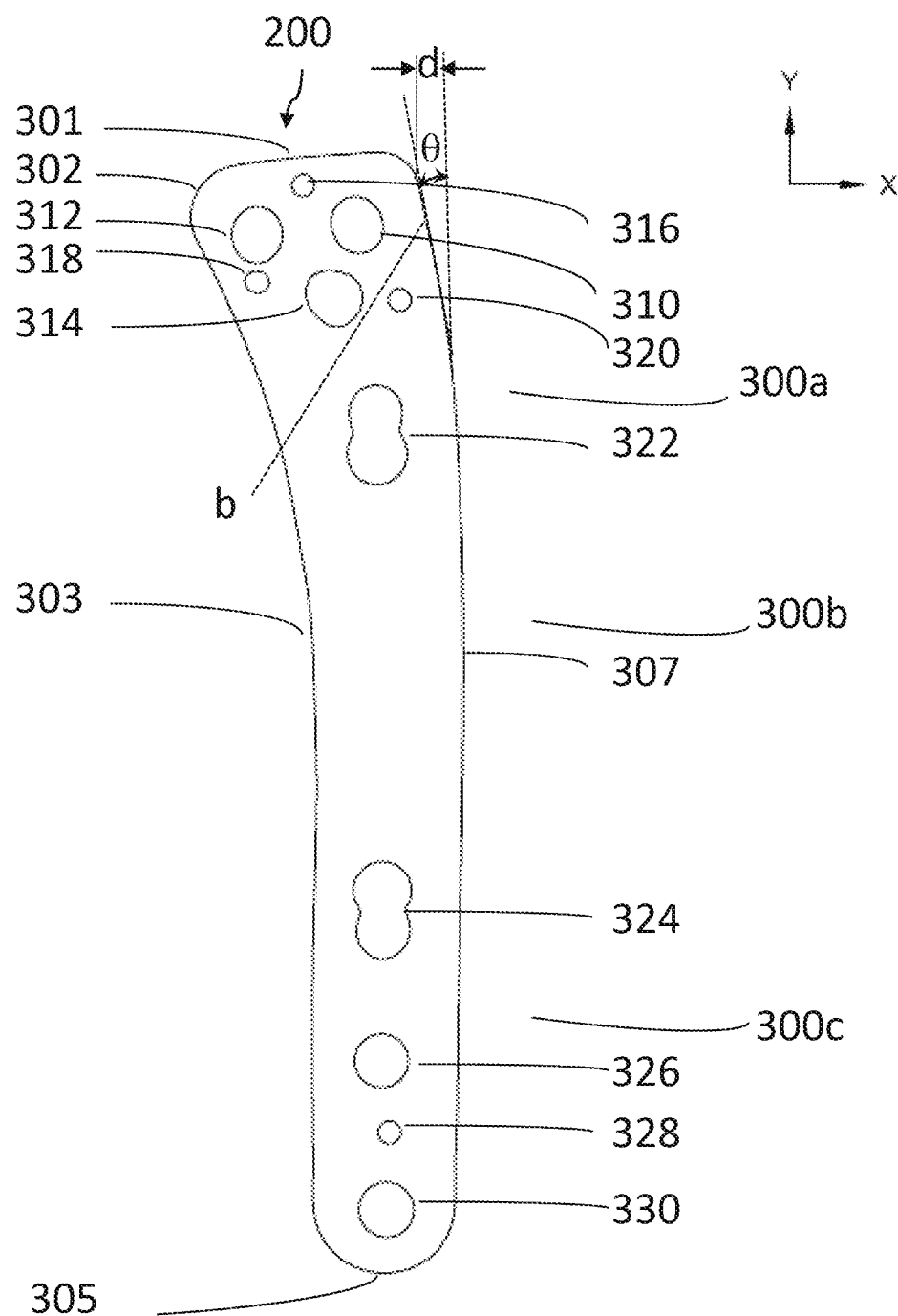
FIG. 2 schematically illustrates a fixation plate for a tibial osteotomy below the tibial tuberosity, according to an embodiment.

Referring to FIG. 2, FIG. 2 schematically illustrates a fixation plate 200, according to an embodiment. The fixation plate 200 is oriented in a manner in which its width direction and length direction, e.g., the elongation direction, are in alignment with the X-axis and Y-axis of the plane of the paper, respectively. The fixation plate 200 can include a top 301, left side 303, bottom 305, and right side 307.

In an embodiment, the shape of the fixation plate 200 looks like a stretched shoe pad with a wide front and a narrow back. The fixation plate 200 can include three portions in an order from the top 301 to the bottom 305: a top-end portion 300a for fixating the portion of the tibia above the surgical cut; a bottom-end portion 300c for fixating the portion of the tibia below the surgical cut; and a connection portion 300b that connects the top-end portion 300a with the bottom-end portion 300c.

The top-end portion 300a has a gradually increasing width toward the top-end 301. The top-end portion 300a can be tilted away from the right side of the connection portion 300b by a degree indicated by an angle θ. In an embodiment, the angle θ is in a range of at or about 0 to at or about 90 degrees. The top-end portion 300a can be offset relative to the right side of the bottom-end portion by distance d. In an embodiment, the distance d is in a range of at or about 0 to at or about 20 mm.

The top-end portion 300a can be capable of fitting the three-dimensional contour of the portion of the tibia above the surgical cut. In an embodiment, the top-end portion 300a is bendable or twistable. In an embodiment, the top-end portion 300a is bent along the approximate line indicated by line b, so that its up-left portion including the edge 302 of the top-end portion 300a is curled or bent out of the plane of the connection portion 300b and the bottom-end portion 300c.

The top-end portion 300a can be provided with a plurality of apertures. In an embodiment, the plurality of apertures can include, but are not limited to, holes. In an embodiment, the holes include through-holes. In an embodiment, the top-end portion 300a has no more than seven through-holes. In an embodiment, the top-end portion 300a has no less than seven through-holes. In an embodiment, the top-end portion 300a has only seven through-holes, including holes 310, 312, 314, 316, 318, 320, and 322. In an embodiment, the seven through-holes are grouped into a first group and a second group. The first group includes the holes 310, 312, 314, 316, 318, and 320, and the second group includes the hole 322. In an embodiment, the first group resides closer to the top-end 301, and the second group resides closer to the connection portion 300b.

The connection portion 300b extends between the top-end portion 300a and the bottom-end portion 300c. In an embodiment, the connection portion 300b extends across the section midway between the top 301 and the bottom 305. In an embodiment, the right side of the connection portion 300b generally has a linear outline. In an embodiment, the right side of the connection portion 300b has a curvilinear profile.

In an embodiment, the connection portion 300b is not provided with a through-hole. In another embodiment, the connection portion 300b is provided with a through-hole.

The bottom-end portion 300c can be strip-shaped. In an embodiment, the left side of the bottom-end portion 300c has a linear outline. In an embodiment, the right side of the bottom-end portion 300c has a linear outline. In an embodiment, the bottom-end portion 300c can have a linear outline at both its left side and right side. The bottom-end 305 is the distal end of the bottom-end portion 300c. In an embodiment, the bottom-end 305 can have a curved profile. In an embodiment, the bottom-end 305 has a semicircular shape.

The bottom-end portion 300c can be provided with a plurality of apertures. In an embodiment, the plurality of apertures includes holes. In an embodiment, the holes include through-holes. In an embodiment, the bottom-end portion 300c has no less than four through-holes. In an embodiment, the bottom end portion 300c has no more than four through-holes. In an embodiment, the bottom-end portion 300c has only four through-holes, including holes 324, 326, 328, and 330.

The holes of the fixation plate 200 can differ in kind, type, and/or shape. The kinds of the holes can include but are not limited to, for example, a screw hole for receiving a screw, pinhole for receiving a guide pin and/or a guidewire, the like, and a combination thereof. The types of holes can include, but are not limited to, for example, threaded hole, non-threaded hole, countersunk hole, counterbored hole, conical hole, truncated conical hole, single hole, Combi hole, oblong hole, the like, and a combination thereof. The shapes of the holes can include, but are not limited to, for example, oblique hole, straight hole, cylindrical hole, elongate hole, circular hole, the like, and a combination thereof.

Figure 3:
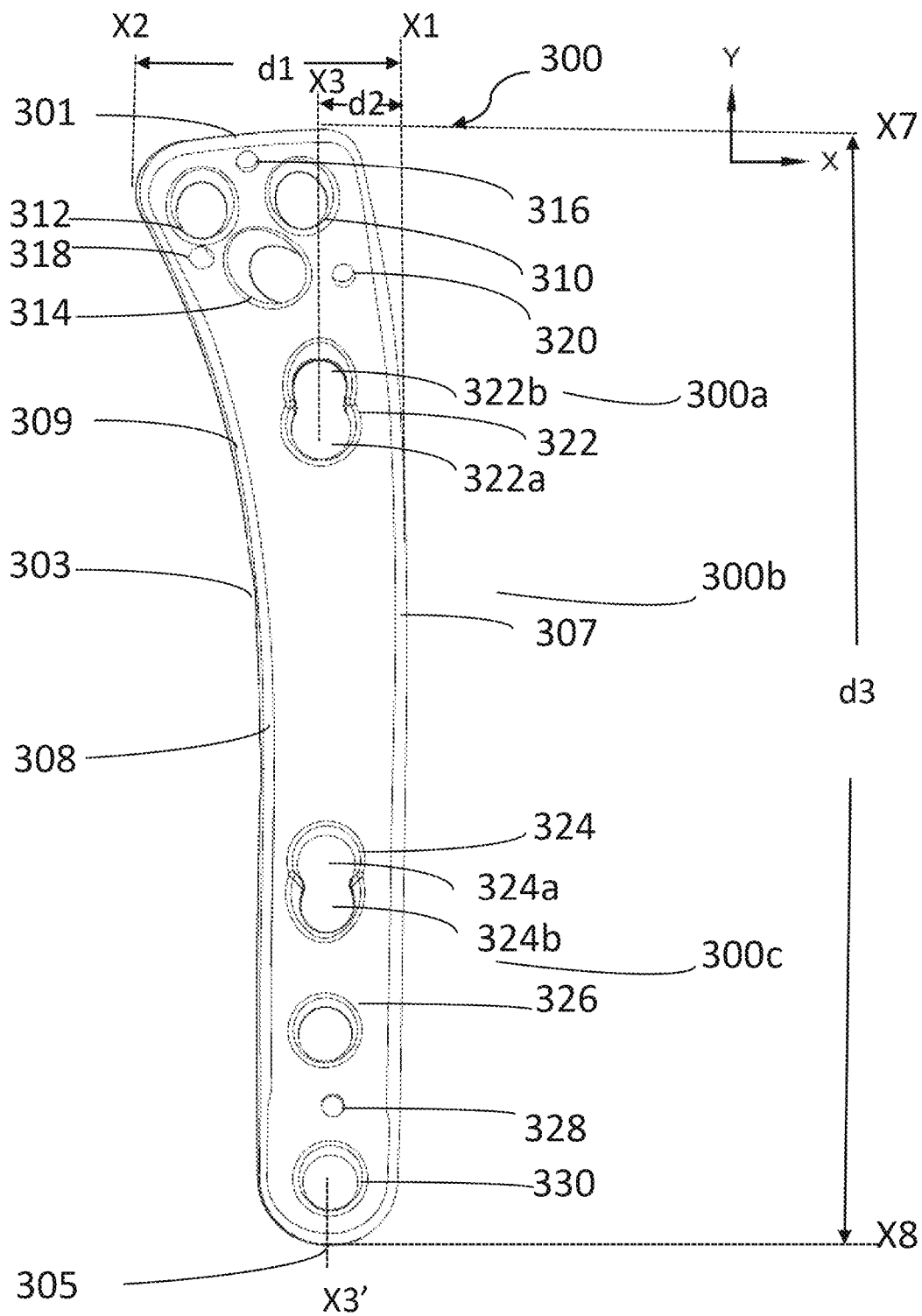
FIG. 3 A schematically illustrates a front view of a fixation plate, according to an embodiment.
Figure 3:
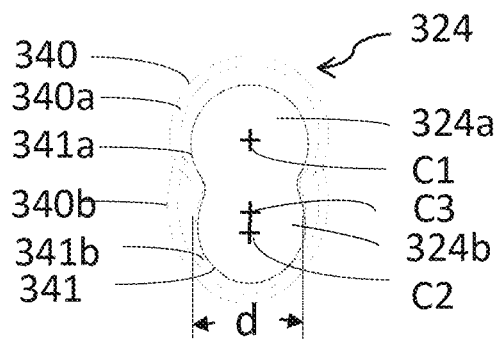
Figure 3:
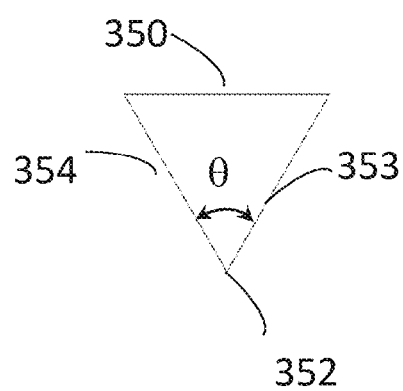
Figure 3:
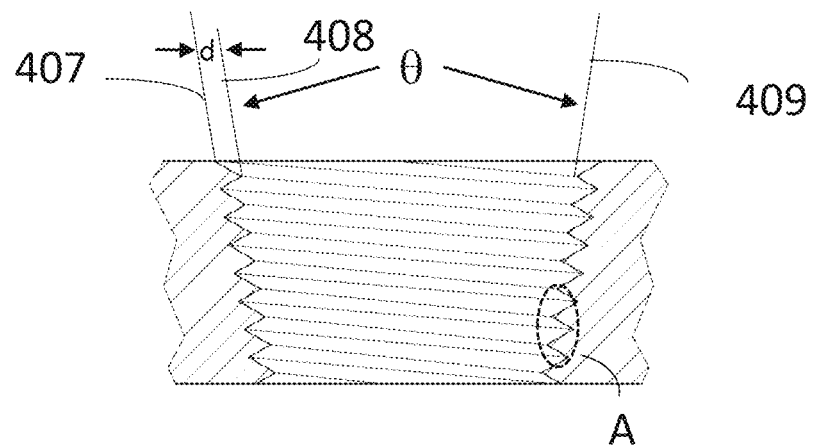
Figure 3:
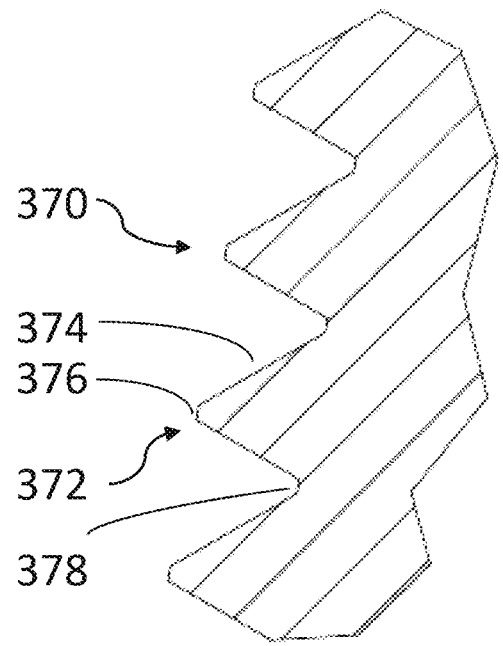
Figure 3:
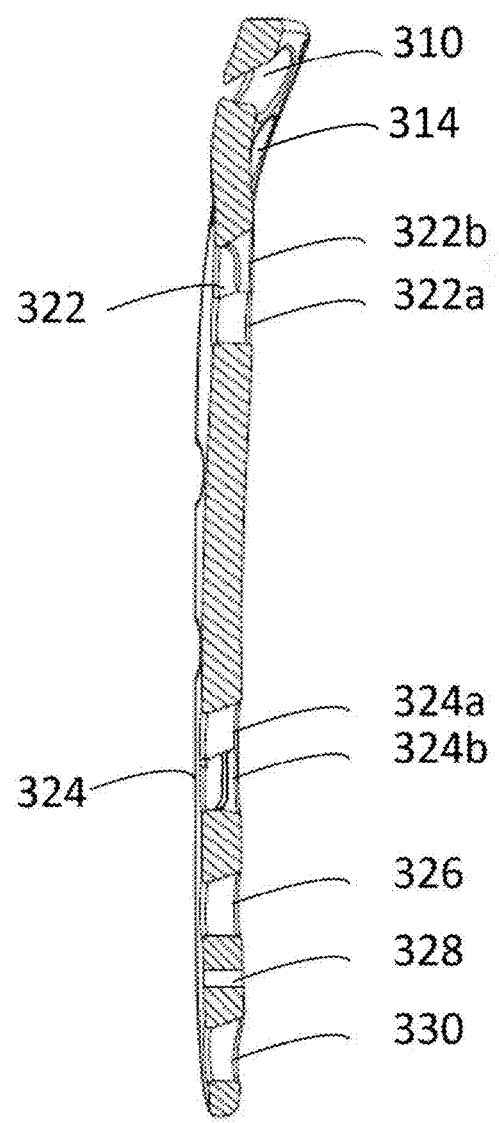

Referring to FIG. 3 A, FIG. 3 A schematically illustrates a front view of a fixation plate 300, according to an embodiment. The fixation plate 300 can be an embodiment of the fixation plate 200 of FIG. 2. For simplicity of the description, features which are the same are labeled with like reference numbers.

The fixation plate 300 can have a curvilinear profile 308. In an embodiment, the top 301, left side 303, bottom 305, and the right side 307 are provided with a smooth, curved surface 309. In an embodiment, the edges that extend between the top 301 and the left side 303, between the left side 303 and the bottom 305, between the bottom 305 and the right side 307, and between the right side 307 and the top 301 are curved. In an embodiment, these edges are provided with a smooth, curved surface.

Referring to the top-end portion 300a in FIG. 3 A, holes 310, 312, 314, and 322 can be screw holes and can receive screws for attaching the fixation plate 300 to the tibia. In an embodiment, the holes 310, 312, and 314 are single, threaded holes. In an embodiment, the arrangement of the holes 310, 312, and 314 adopts a triangular configuration, as lines drawn between their centers resemble a triangle. In an embodiment, the arrangement of the holes 310, 312, and 314 adopts an oblique triangle configuration. In an embodiment, the arrangement of the holes 310, 312, and 314 is an inverted triangle configuration, in which the holes 310 and 312 are closer to the top 301 than the hole 314. In an embodiment, the holes 310 and 312 are arranged parallel to the top 301, with an equal distance to the top 301. In an embodiment, the center of the hole 314 has an equal distance to the centers of the holes 310 and 312. In an embodiment, the centers of the hole 310, 312, and 314 are at equal distance from each other.

It is appreciated that the arrangement of the holes 310, 312, and 314 can adopt other suitable configurations other than the inverted triangle configuration.

Each of the holes 310, 312, and 314 can be configured to various types and shapes suitable for accommodating different types of screws they receive. In an embodiment, one or more of the holes 310, 312, and 314 are conical holes. In an embodiment, one or more of the holes 310, 312, and 314 are countersunk hole. In an embodiment, one or more of the holes 310, 312, and 314 are threaded holes. In an embodiment, one or more of the holes 310, 312, and 314 are oblong holes. In an embodiment, two or more of the holes 310, 312, and 314 are identical to each other. In an embodiment, two or more of the holes 310, 312, and 314 are not identical to each other. In an embodiment, the holes 310 and 312 are identical to each other. In an embodiment, the holes 310, 312, and 314 are identical to each other. In an embodiment, the holes 310, 312, and 314 differ in screw thread, for example, number and type of the thread.

In an embodiment, the holes 316, 318, and 320 can be pinholes for receiving a guidewire and/or a pin. Each of these holes can be disposed between two of the holes 310, 312, and 314. In an embodiment, the holes 310, 316, 312, 318, 314, and 320 are arranged alternately. For example, the hole 316 can be disposed between the holes 310 and 312, the hole 318 can be disposed between the holes 312 and 314, and the hole 320 can be disposed between the holes 314 and 310. In an embodiment, these holes are for temporary k-wire fixation.

The hole 316 can be closer to the top-end 301 than the holes 318 and 320, which forms a triangular configuration. In an embodiment, the hole 316 can reside below the middle of the top-end 301. In an embodiment, the holes 316, 318, and 320 are outside the triangle formed by drawing lines between the centers of the holes 310, 312, and 314.

In an embodiment, each of the holes 310, 312, 314, 316, 318, and 320 can have a circular or oval opening. In an embodiment, one or more of the holes 310, 312, 314, 316, 318, and 320 have circular openings. In an embodiment, one or more of the holes 310, 312, 314, 316, 318, and 320 have an oval opening. In an embodiment, the hole 314 has an oval opening. In an embodiment, each of the holes 316, 318, and 320 has an oval opening. The oval opening allows a screw or guide pin to be inserted at an angle that is not perpendicular to the plate. In an embodiment, the oval opening prevents the inserting screw from penetrating out and reaching the fibula joint. In an embodiment, each of the holes 316, 318, and 320 has a circular opening.

In an embodiment, the hole 322 is a Combi hole. A Combi hole is a combination of two or more overlapping holes. Each of the overlapping holes can be a hole section of the Combi hole. In an embodiment, the hole 322 includes two hole sections 322a and 322b. In an embodiment, the hole section 322b is above the hole section 322a. In an embodiment, the hole section 322b stacks on the top of the hole section 322a. In an embodiment, the orientation of the hole 322 can be indicated by the line X3 formed by connecting the centers of the hole sections 322a and 322b. In an embodiment, the orientation of the hole 322 is along the length direction of the fixation plate 300, as the line X3 is parallel to the length direction indicated by line X1.

In an embodiment, at least one of the hole sections 322a and 322b has a conical frustum shape. In an embodiment, the hole sections 322a and 322b contain a cylindrical portion. In an embodiment, the hole sections 322a and 322b are cylindrical. In an embodiment, the hole sections 322a and 322b have the same radius. In an embodiment, the hole sections 322a and 322b have different radii. In an embodiment, the hole section 322a is smaller in radius than the hole section 322b. In an embodiment, the hole section 322a is larger in radius than the hole section 322b. In an embodiment, the hole sections 322a and 322b of the hole 322 can have a radius in a range of at or about 0.25 mm to at or about 4 mm. In an embodiment, the hole sections 322a and 322b can have a radius of at or about 0.5 mm. It is appreciated that the hole sections 322a and 322b can be configured to any suitable radius for accommodating the screws or pins they receive.

In an embodiment, one of the hole sections 322a and 322b is a threaded hole section, and the other one is a DCP hole section. The DCP hole section does not contain thread and can receive a standard screw, for example, cortex screw. The threaded hole section can receive a locking head screw. In an embodiment, the hole section 322a is a threaded hole, and the hole section 322b is a DCP hole. In an embodiment, the hole section 322a is a DCP hole, and the hole section 322b is a locking screw hole.

The sizes of the holes 310, 312, 314, 316, 318, 320, and 324 can be configured to accommodate the screws or guide pins that they receive. In an embodiment, the holes 310, 312, and 314, which accept screws, generally are larger in dimension than the holes 316, 318, and 320, which accept guide pins or wires.

The sizes of the holes 310, 312, and 314 can be different from or identical to each other. In an embodiment, the sizes of the holes 310, 312, and 314 can be identical to each other and have a diameter of in a range of at or about 1 mm to at or about 8 mm.

The sizes of the holes 316, 318, and 320 can be different from or identical to each other. In an embodiment, the sizes of the holes 316, 318, and 320 are identical to each other and have a radius in a range of at or about 0.5 mm to at or about 4 mm. In an embodiment, each of the holes 316, 318, and 320 are smaller than any of the holes 310, 312, and 314 in dimension or diameter. In an embodiment, the holes 316, 318, and 320 have a dimension or diameter similar or identical to those of the holes 310, 312, and 314.

Referring to the connection portion 300b, the connection portion 300b can have a length in a range of at or about 1 to at or about 50 mm, according to an embodiment. In an embodiment, the lower limit of the range of the length can be at or about 10 mm, at or about 15 mm, at or about 20 mm, at or about 25 mm, at or about 30 mm, or at or about 35 mm. In an embodiment, the upper limit of the range of the length can be at or about 30 mm, at or about 35 mm, at or about 40 mm, at or about 45 mm, or at or about 50 mm. It is appreciated that the above range of the length of the connection portion 300b is exemplary, and the connection portion 300b can adopt any suitable length depending on the specific patient.

Referring to the bottom-end portion 300c, the holes 324, 326, 328, and 330 can be arranged in an order from top to bottom. In an embodiment, the holes 324, 326, 328, and 330 are arranged along the length direction of the fixation plate 300. In an embodiment, the holes 324, 326, 328, 330, and 322 are situated on a line along the length direction but not necessarily through their centers. In an embodiment, the centers of the holes 324, 326, 328, 330, and 322 are not situated on the line. In an embodiment, the centers of the holes 324, 326, 330, and 322 are situated on the line, but the center of the hole 328 is not situated on the line. In an embodiment, the centers of the holes 324, 326, 328, 330, and 322 are situated on the line. In an embodiment, the line is the middle-width line of the bottom-end portion 300c, indicated by the line X3'.

As with the hole 322, the hole 324 can be a Combi hole. In an embodiment, the hole 324 includes two hole sections 324a and 322b. In an embodiment, the hole section 322a is above the hole section 322b. In an embodiment, the hole section 322a stacks on the top of the hole section 322b. In an embodiment, the hole sections 324a and 324b can have the same radius. In an embodiment, the hole sections 324a and 324b can have different radii. In an embodiment, the hole section 324a can have a smaller radius than the hole section 324b. In an embodiment, the hole section 324a can have a larger radius than the hole section 322b. In an embodiment, each of the hole sections 324a and 324b has a radius in a range of at or about 0.25 mm to at or about 4 mm. In an embodiment, the hole sections 324a and 324b can have a radius of at or about 0.5 mm. It is appreciated that the hole sections 324a and 324b can be configured to any suitable radius for accommodating the screws or pins they receive.

In an embodiment, one of the hole sections 324a and 324b is a threaded hole section, and the other is a DCP hole section. In an embodiment, the hole section 324a is a threaded hole section, and the hole section 324b is a DCP hole section.

The holes 322 and 324 are the two holes closest to the connection portion 300b, where the midsection of the fixation plate 300 resides. In an embodiment, the connection portion 300b generally extends over the surgical cut of the tibial osteotomy, and the screws going through the holes 322 and 324 can provide direct fixation force. In an embodiment, the holes 322 and 324 are identical to each other and oriented in a head to head manner so that the compression of the two Combi holes is directed toward the middle of the fixation plate 300. In an embodiment, the hole 324 and the hole 322 relate to each other by a reflection symmetry between the hole 324 and the hole 322. The holes 322 and 324 can provide the flexibility of axial compression and locking capability. In an embodiment, the hole sections 322a and 324a are threaded holes, and the hole sections 322b and 324b are DCP holes.

In an embodiment, the hole section 322a and 324a contain thread where the screw is inserted to hold the fixation plate 300 onto the tibia. After that, a locking screw can be put in each of the hole sections 322b and 324b. In an embodiment, none of the screws at holes 322a/322b and 324a/324b goes in/through the cut 20 shown in FIGS. 1 and 2, during and after the operation of the tibial osteotomy below the tibial tuberosity. In an embodiment, none of the screws received by the holes 322 and 324 penetrates the osteotomy cut after the operation of the tibial osteotomy below the tibial tuberosity.

The holes 326 and 330 can be screw holes for receiving screws. The hole 326 can be the same as or different from the hole 330. In an embodiment, each of the holes 326 and 330 can accept only a locking head screw. In an embodiment, the holes 326 and 330 contain no thread and accept standard screws, for example, cortex screws. In an embodiment, the holes 326 and 330 are threaded holes and accept locking head screws. In an embodiment, at least one of the holes 326 and 330 are threaded holes for receiving a locking head screw. In an embodiment, the hole 330 is a threaded hole for accepting a locking head screw. In an embodiment, the hole 330 is not a threaded hole, and the hole 330 accepts a cortex screw. In an embodiment, the hole 326 is a threaded hole for accepting a locking head screw. In an embodiment, the hole 326 is not a threaded hole, and the hole 326 accepts a cortex screw.

The holes 326 and 330 can be conical holes. However, it is understood that the holes 326 and 330 each can independently be configured to the various types and shapes of holes, depending on the screws they accept. In an embodiment, the holes 326 and 330 each can independently be a countersunk hole or counterbored hole. In an embodiment, the holes 326 and 330 each can independently be an oblong hole or a circular hole.

The holes 326 and 330 can be identical to or different from each other in dimension or diameter. In an embodiment, the holes 326 and 330 have a diameter in a range of at or about 3 to at or about 6 mm.

In an embodiment, the holes 326 and 330 can have openings. In an embodiment, the shapes of the openings can include, but are not limited to, circle and oval. In an embodiment, the openings of the holes 326 and 330 each can independently be circular.

The hole 328 can be a pinhole for receiving a guide pin or guidewire. In an embodiment, the hole 328 is smaller than each of the holes 324, 326, and 330 in dimension or diameter. In an embodiment, the dimension or diameter of the hole 328 is similar or identical to those of the holes 324, 326, and 330. In an embodiment, the hole 328 can be a cylindrical hole having a circular opening.

In an embodiment, the holes 326, 330, 310, 312, and 314 are identical to each other and receive the same screws. In an embodiment, the holes 328, 316, 318, and 320 are identical to each other.

The dimension of the fixation plate 300 can be patient-specific. The top-end portion 300a can have a width d1, which is the distance between lines X1 and X2. In an embodiment, the width d1 is in a range of at or about 27.3 mm to at or about 27.7 mm. In an embodiment, the width d1 is at or about 27.5 mm. The hole 322 can be away from line X1 by a distance d2, which is the distance between lines X1 and X3. The line X3 is a line drawn along centers of the hole sections 322a and 322b. In an embodiment, the distance d2 is in a range from at or about 8.75 to at or about 8.9 mm. In an embodiment, the distance d2 is at or about 8.75±0.02 mm. The fixation plate 300 can have a length d3 indicated by the distance between lines X7 and X8. In an embodiment, length d3 is in a range of at or about 90 mm to at or about 250 mm. In an embodiment, the length d3 is in a range of at or about 100 mm to at or about 160 mm. In an embodiment, the length d3 is at or about 111.5±0.5 mm. In an embodiment, the length d3 is at or about 111.5 mm. In an embodiment, the length d3 is at or about 112.8±0.5 mm. In an embodiment, the length d3 is at or about 112.8 mm. It is appreciated that the above values/ranges of the width d1, the distance d2, and the length d3 are exemplary and can be any suitable values/ranges depending on a specific patient.

Referring to FIG. 3 B, FIG. 3 B schematically illustrates openings of the hole 324 of FIG. 3 A, according to an embodiment. The hole 324 can include a front opening 340 and a back opening 341. The front opening 340 of the hole 324 can be divided into front opening 340a and front opening 340b in accordance with its hole sections. Likewise, the back opening 341 of the hole 324 can be divided into back opening 341a and back opening 341b according to its hole sections. In other word, the hole section 324a includes the front opening 340a and the back opening 341a, and the hole section 324b includes the front opening 340b and the back opening 341b. In an embodiment, the back openings 341a and 341b have the same diameter in a range of at or about 5.34 mm to at or about 5.5 mm. The center of the back opening 341a and the center of the back opening 341b are indicated by C1 and C2, respectively. The center of the front opening 340b is indicated by C3. In an embodiment, the distance between C1 and C3 is at or about 4.52 mm. In an embodiment, the distance between C3 and C2 is at or about 0.9 mm. In an embodiment, at least one of the hole sections 324a and 324b includes a truncated conical hole. In an embodiment, both of the hole sections 324a and 324b include a truncated conical hole. It is appreciated that the hole sections 324a and 324b can adopt suitable shapes other than a truncated conical shape. In an embodiment, at least one of the hole sections 324a and 324b include a cylindrical hole. In an embodiment, both of the hole sections 324a and 324b include a cylindrical hole. In an embodiment, the hole section 324a includes a threaded hole. In an embodiment, the hole section 324b includes a DCP hole. It is appreciated that the hole 322 can also have the features described in this paragraph.

Referring to FIG. 3 C, FIG. 3 C schematically illustrates the angle of the hole 330 of FIG. 3 A, relative to center 352 of the bottom 305 of the fixation plate 300, according to an embodiment. The center 352 is an imagined center point of the bottom 305 of the fixation plate 300. Diameter 350 is the diameter of the hole 330 at the width direction of the fixation plate 300. Lines 353 and 354 are lines drawn from the center 352 to the ends of the diameter 350. The angle θ between the lines 353 and 354 represents the angle of the hole 330 relative to the center 352. In an embodiment, the angle θ is in a range of at or about 59.8° to at or about 60.2°. In an embodiment, the angle θ is at or about 60.0°.

Referring to FIG. 3 D, FIG. 3 D schematically illustrates the A-A section of the hole 330 of FIG. 3 A, according to an embodiment. The hole 330 can be a conical double lead thread hole. In an embodiment, the conical double lead thread hole has a pitch of at or about 0.5 mm, a thread thickness of at or about 0.425 mm indicated by the distance d between lines 407 and 408, and a flat land of at or about 0.1 mm to at or about 0.2 mm. The hole 330 can have a cone angle of at or about 20.0°±0.2°, as indicated by the angle θ between lines 408 and 409. In an embodiment, the features of the hole 330 discussed in this paragraph are shared by the holes 310, 312, 314, and 326.

Referring to FIG. 3 E, FIG. 3 E schematically illustrates an enlarged view of portion A of FIG. 3 D, according to an embodiment. FIG. 3 E illustrates thread 370 of the hole 330. The thread 370 can include screw thread 372. The screw thread 372 can include flank 374, crest 376, and root 378. The flank 374 is the portion of the surface on either side of the screw thread 372. The root 378 is the bottom edge of the thread 370, connecting the adjacent flank 374 at the bottom of the thread 370. The crest 376 is the top edge of the thread 370, connecting the adjacent flank 374 of the thread 372. The crest 376 can be a flat surface referred to as flat land. The flat land can prevent the crest 376 from breaking while contacting a screw, as compared to a conventional sharp "V" thread form.

Referring to FIG. 3 F, FIG. 3 F schematically illustrates a cross-section of the fixation plate 300 of FIG. 3 A along the line X3, according to an embodiment. In an embodiment, the line X3 is in alignment with the middle-width line X3' of the bottom-end portion 300c in FIG. 3 A. The fixation plate 300 can generally have a thickness of at or about 4.0 mm. In an embodiment, the fixation plate 300 has an identical or substantially similar thickness from top to bottom. From top to bottom of this view, the holes in FIG. 3 F can be the screw hole 310, screw hole 314, Combi hole 322, Combi hole 324, screw hole 326, pinhole 328, and screw hole 330. In an embodiment, the Combi holes 322 and 324 are the ones nearest to the midsection of the fixation plate 300 and provide compression force for fixating the osteotomy.

Figure 4:
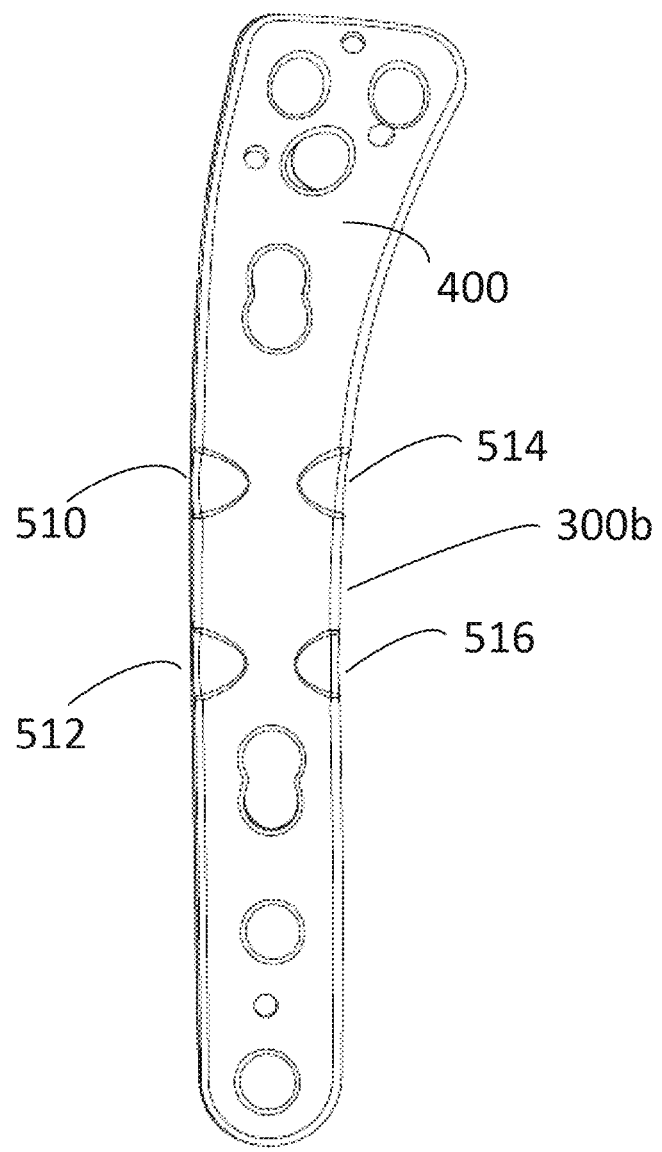
FIG. 4 schematically illustrates a rear view of the fixation plate of FIG. 3 A, according to an embodiment.

Referring to FIG. 4, FIG. 4 schematically illustrates a rear view of the fixation plate 300 of FIG. 3 A, according to an embodiment. The rear 400 faces the tibia. A plurality of recesses, including recesses 510, 512, 514, and 516, can be provided at both sides of the rear of the connection portion 300b. In an embodiment, one or more of the recesses are grooves. These recesses can improve blood supply to the bone area under the fixation plate 300. These recesses can reduce the pressure of the fixation plate 300 on the blood vessels.

Figure 5:
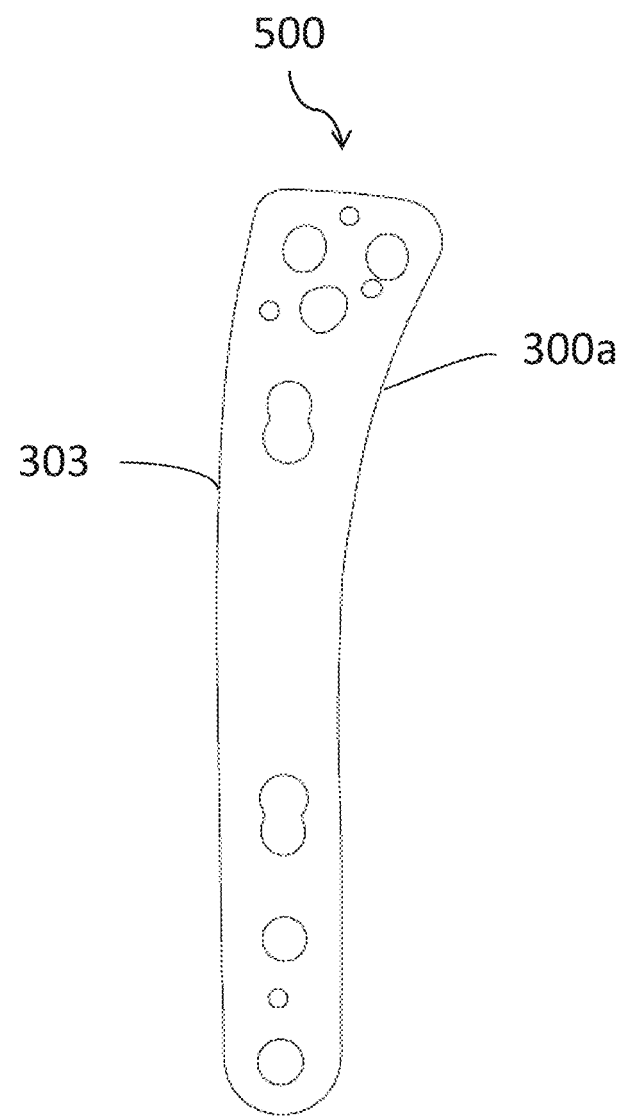
FIG. 5 schematically illustrates a fixation plate for a tibial osteotomy below the tibial tuberosity, according to another embodiment.

Referring to FIG. 5, FIG. 5 illustrates a fixation plate 500 for tibial osteotomy below the tibial tuberosity, according to another embodiment. The fixation plate 500 differs from the fixation plate 200 or 300 in that the top-end portion 300a of the fixation plate 500 is tilt away from the left side 303 of the fixation plate 500. The fixation plate 500 can be useful in the tibial osteotomy of the right leg, and the fixation plate 200 or 300 can be useful in the tibial osteotomy of the left leg. The fixation plate 500 can have structural features substantially identical or similar to those of the fixation plate 200 or 300 described herein. In an embodiment, the fixation plates 200, 300, and 500 are medial tibial fixation plates. In an embodiment, the fixation plates 200, 300, and 500 are lateral tibial fixation plates.

Figure 6:
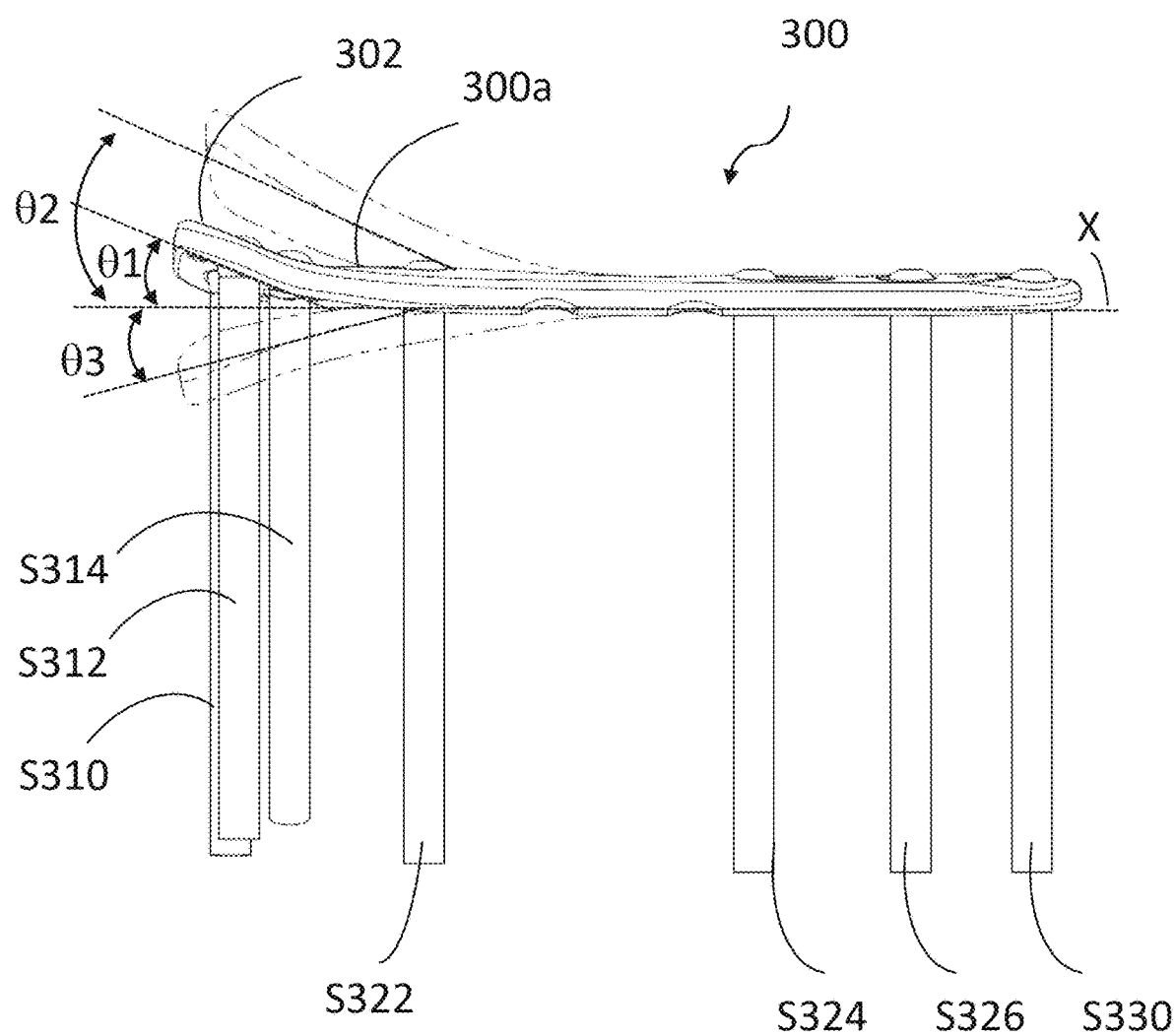
FIG. 6 schematically illustrates an installation of the fixation plate of FIG. 3 A, according to an embodiment.

Referring to FIG. 6, FIG. 6 schematically illustrates an installation of the fixation plate 300 of FIG. 3 A, according to an embodiment. The fixation plate 300 fixates bone portions at both sides of the cut, for example, the cut 20 in FIG. 1, with screws. The screws installed into holes 310, 312, 314, 322, 324, 326, and 330 of the fixation plate 300 are referred to as S310, S312, S314, S322, S324, S326, and S330, respectively. The length direction of the fixation plate 300 is indicated by line X. The screw S330 is generally perpendicular to the length direction.

The fixation plate 300 is capable of fitting a surface contour of the tibia where it is attached. In an embodiment, the fixation plate 300 is manufactured to a shape conforming to the contour of the tibia. In an embodiment, the fixation plate 300 is capable of retrofitting the surface contour of the tibia. In an embodiment, the fixation plate 300 is bendable or twistable to fit the surface contour of the tibia where it is attached. In an embodiment, the edge 302 of the top-end portion 300a of the fixation plate 300 is curled or bent out of the plane of the connection portion 300b and the bottom-end portion 300c along, for example, the line b indicated in FIG. 2, resulting in an angle of θ1 relative to the line X. In an embodiment, the angle of θ1 is in a range of at or about −2° to at or about +2°. When the angle of θ1 is above 0, the edge 302 is curled or bent above the line X, viewed from FIG. 6. When the angle of θ1 is below 0, the edge 302 is curled or bent below the line X, viewed from FIG. 6. In an embodiment, the angle of θ1 is in a range of at or about −5° to at or about +5°. In an embodiment, the angle of θ1 is in a range of at or about −8° to at or about +8°. In an embodiment, the angle of θ1 is in a range of at or about −10° to at or about +10°. In an embodiment, the angle of θ1 is in a range of at or about −15° to at or about +15°. In an embodiment, the θ1 is in a range of at or about −20° to at or about +20°.

In an embodiment, the top-end portion 300a of the fixation plate 300 is curled or bent out the plane of the connection portion 300b and the bottom-end portion 300c, resulting in an angle of θ2 or θ3 relative to the line X. The angle of θ2 indicates that the top-end portion 300a of the fixation plate 300 is curled or bent above the plane of the connection portion 300b and the bottom-end portion 300c, viewed from FIG. 6. The angle of θ3 indicates that the top-end portion 300a of the fixation plate 300 is curled or bent below the plane of the connection portion 300b and the bottom-end portion 300c, viewed from FIG. 6. In an embodiment, the θ2 and θ3 are in a range of at or about 0° to at or about 5°. In an embodiment, the θ2 and θ3 are in a range of at or about 5° to at or about 10°. In an embodiment, the θ2 and θ3 are in a range of at or about 10° to at or about 15°. In an embodiment, the θ2 and θ3 are in a range of at or about 15° to at or about 20°.

Figure 7:
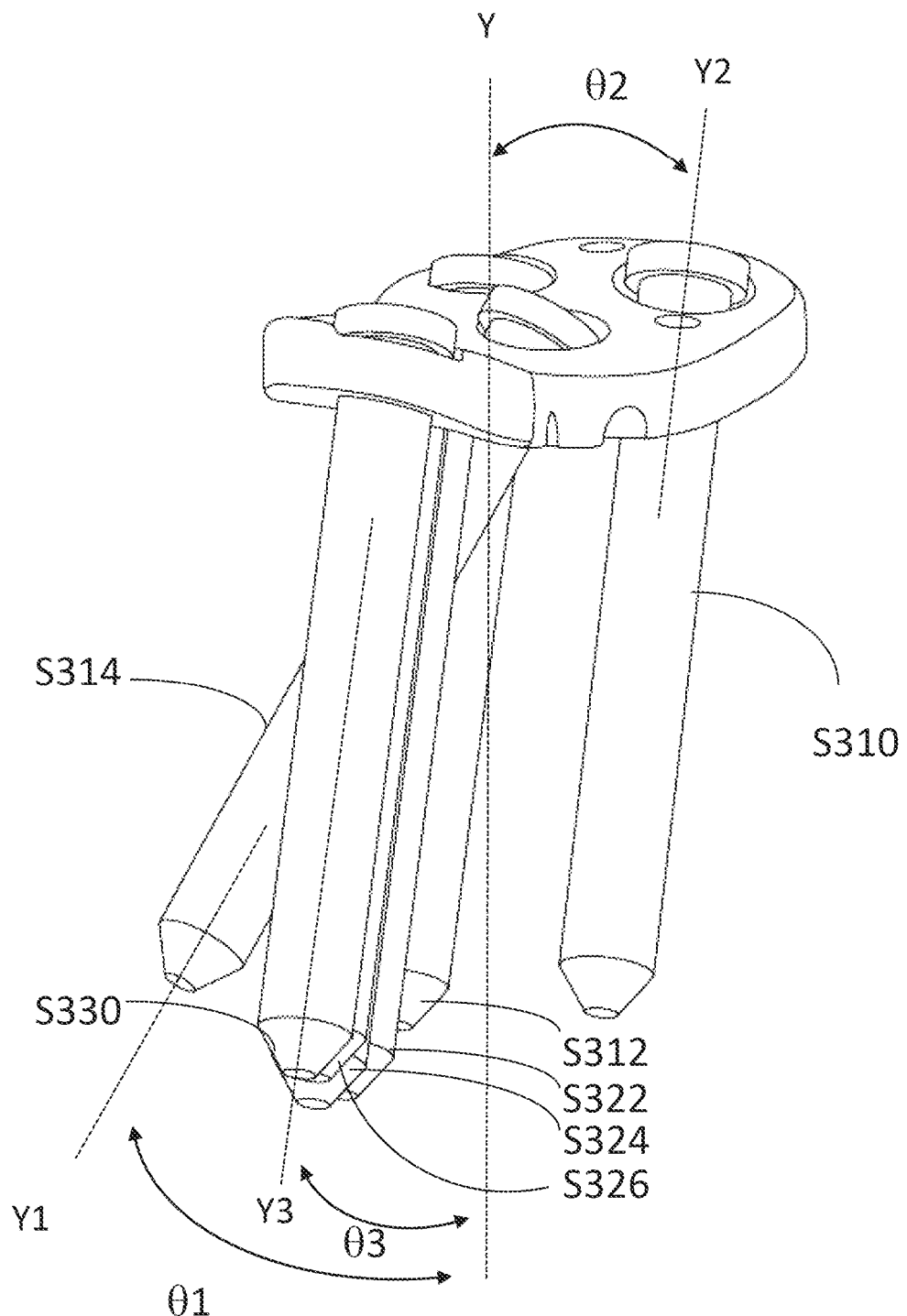
FIG. 7 schematically illustrates an installation of screws of the fixation plate of FIG. 6, according to an embodiment.

Referring to FIG. 7, FIG. 7 schematically illustrates an installation of screws to the fixation plate 300, according to an embodiment. Line Y generally perpendicular to the main plane of the fixation plate 300 and line X in FIG. 6. Line Y1, Y2, and Y3 indicate the extension direction of the screws S314, S310, and S330, respectively. In an embodiment, the screws S322, S324, S326, and S330 are generally parallel to each other. In an embodiment, the screw S330 is angled at or about 7.36° relative to line Y, indicated by the angle of θ3 between Lines Y3 and Y. In an embodiment, the screws S322, S324, and S326 are angled at or about 7.36° relative to line Y. In an embodiment, the screw S314 is angled at or about 32.45° relative line Y, indicated by the angle of θ1 between Lines Y1 and Y. In an embodiment, the screw S310 is angled at or about 6.4° relative line Y, indicated by the angle of θ2 between Lines Y2 and Y. It is appreciated that the screws described herein can adopt other suitable angles relative to line Y.

Figure 8:
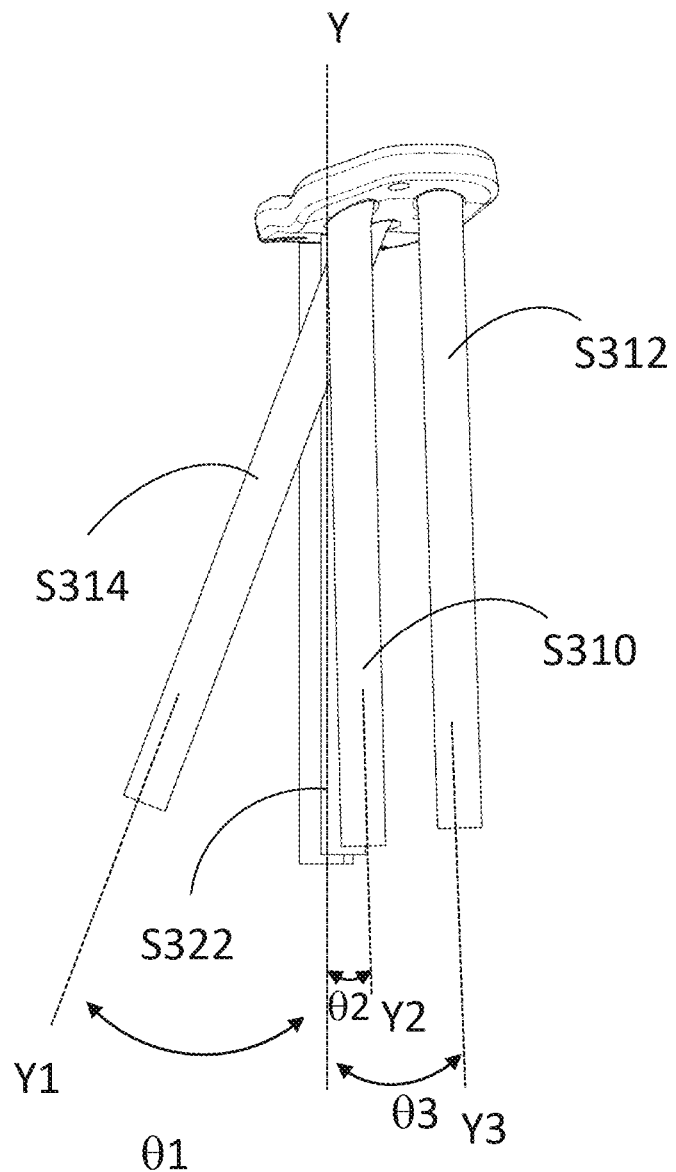
FIG. 8 schematically illustrates an installation of screws of the fixation plate of FIG. 6, according to another embodiment.

Referring to FIG. 8, FIG. 8 schematically illustrates an installation of screws to the fixation plate 300, according to another embodiment. Line Y is perpendicular to the main plane of the fixation plate 300 as shown in FIG. 8. In an embodiment, the screw 322 is oriented parallel to line Y. In an embodiment, the screw 324 is also oriented parallel to line Y. Lines Y1, Y2, and Y3 are along the extension directions of the screws S314, S310, and S312, respectively. In an embodiment, the screw S314 is angled at or about 20.912° relative to line Y, indicated by θ1 between lines Y1 and Y. In an embodiment, the screw S310 is angled at or about 1.345° relative to line Y, indicated by θ2 between lines Y2 and Y. In an embodiment, the screw S312 is angled at or about 1.802°, indicated by θ3 between lines Y3 and Y. It is appreciated that the screws described herein can adopt other suitable angles relative to line Y. In an embodiment, the angle between the screws S322 and S314 is at or about 20.912°. In an embodiment, the angle between the screws S322 and S310 is at or about 1.345°. In an embodiment, the angle between the screws S322 and S312 is at or about 1.802°.

Aspects

Any one of aspects 1-23 is combinable to any one of aspects 24-28.

Aspect 1. A fixation plate for internal fixation of an osteotomy below the tuberosity of a tibia, comprising an elongated body including a top end and a bottom end opposing the top end along the length direction of the elongated body,
wherein the elongated body, viewed from the top end to the bottom end, comprises:
a top-end portion comprising a first pinhole, a second pinhole, a third pinhole, a first screw hole, a second screw hole, a third screw hole, and a first Combi hole;
a bottom-end portion comprising a second Combi hole, a first screw hole, a pinhole, and a second screw hole; and
a connection portion connecting the top-end portion with the bottom-end portion,
wherein the third screw hole of the top-end portion is disposed below the first and the second screw holes of the top-end portion.

Aspect 2. The fixation plate of aspect 1, wherein the first, second, and third screw holes of the top end portion are arranged in an inverted triangular configuration.

Aspect 3. The fixation plate as in any one of aspects 1-2, wherein each of the first, second, and third pinholes of the top-end portion is disposed between two of the first, second, and third screw holes of the top-end portion.

Aspect 4. The fixation plate as in any one of aspects 1-3, wherein the first pinhole, the second pinhole, and the third pinhole of the top-end portion alternate with the first screw hole, the second screw hole, and the third screw hole of the top-end portion.

Aspect 5. The fixation plate as in any one of aspects 1-4, wherein the first Combi hole is disposed closer to the connection portion than the screw holes and pinholes of the top-end portion.

Aspect 6. The fixation plate as in any one of aspects 1-5, wherein the connection portion is not provided with a through-hole.

Aspect 7. The fixation plate as in any one of aspects 1-6, wherein the second Combi hole is disposed closer to the connection portion than the screw holes and pinhole of the bottom-end portion.

Aspect 8. The fixation plate as in any one of aspects 1-7, wherein each the first and the second Combi hole includes two hole sections.

Aspect 9. The fixation plate as in aspect 8, wherein one of the hole sections is a threaded hole section, and the other is a DCP hole section.

Aspect 10. The fixation plate as in any one of aspects 1-9, wherein the first and second Combi holes are identical to each other and oriented in a head to head manner.

Aspect 11. The fixation plate as in any one of aspects 1-10, wherein the first and the second Combi holes have an orientation parallel to the length direction of the fixation plate.

Aspect 12. The fixation plate as in any of aspects 1-11, wherein at least one of the first and the second screw holes of the bottom-end portion is a conical frustum hole.

Aspect 13. The fixation plate as in any one of aspects 1-12, wherein the second screw hole of the bottom-end portion is disposed below the first screw hole of the bottom-end portion, and the second screw hole of the bottom-end portion is a double lead conical thread hole having a pitch of at or about 0.5 mm, a thread thickness of at or about 0.425 mm, and a cone degree of at or about 18.8° to at or about 20.2°.

Aspect 14. The fixation plate as in any one of aspects 1-13, wherein the second screw hole of the bottom-end portion is disposed below the first screw hole of the bottom-end portion, and the second screw hole of the bottom-end portion has an angle of at or about 59.8° to 60.2° relative to the center of the bottom-end.

Aspect 15. The fixation plate as in any one of aspects 1-14, wherein the pinhole of the bottom-end portion situates between the first and the second screw holes of the bottom-end portion.

Aspect 16. The fixation plate as in any one of aspects 1-15, wherein the first Combi hole, the second Combi hole, the first and the second screw holes of the bottom-end portion, and the pinhole of the bottom-end portion are in alignment with the middle-width line of the bottom-end portion.

Aspect 17. The fixation plate as in any one of aspects 1-16, wherein the bottom-end portion has a strip shape and is narrower than the top-end portion in width.

Aspect 18. The fixation plate as in any one of aspects 1-17, wherein the bottom-end portion is capable of fixating the portion of the bone below a cut of the osteotomy of the tibia, and the top-end portion is capable of fixating the portion of the bone above the cut.

Aspect 19. The fixation plate as in any one of aspects 1-18, wherein the fixation plate has a length in a range of at or about 111 mm to at or about 112 mm.

Aspect 20. The fixation plate as in any one of aspects 1-19, wherein the top-end portion has a width in a range of at or about 27.3 mm to at or about 27.7 mm, and the bottom-end portion has a width in a range of at or about 17.3 mm to at or about 17.7 mm.

Aspect 21. The fixation plate as in any one of aspects 1-20, wherein the fixation plate is capable of fitting the three-dimensional contour of the tibia around a cut of the osteotomy.

Aspect 22. The fixation plate as in any one of aspects 1-21, wherein the top-end portion is bendable or twistable to fit the three-dimensional contour of the tibia.

Aspect 23. The fixation plate as in any one of aspects 1-22, wherein the top-end portion is laterally offset relative to the bottom-end portion.

Aspect 24. A tibial osteotomy below the tibial tuberosity, comprising;
cutting a tibia at a site below the tibial tuberosity to obtain a cut tibia; and
fixating the cut tibia with a fixation plate as in any one of aspects 1-23.

Aspect 25. The tibial osteotomy below the tibial tuberosity as in aspect 24, further comprising realigning the cut tibia.

Aspect 26. The tibial osteotomy below the tibial tuberosity as in any one of aspects 24-25, wherein cutting the tibia includes prying the cut of the tibia open to obtain a wedge-shaped opening.

Aspect 27. The tibial osteotomy below the tibial tuberosity as in any one of aspects 24-26, wherein fixating the cut tibia with a fixation plate includes installing screws into the first, second, and third screw holes of the top-end portion and the first and second screw holes of the bottom-end portion, respectively,
wherein the screws at the second Combi hole, the first screw hole, and the second screw hole of the bottom-end portion are generally parallel to each other, and are angled at or about 7.36° relative to a line that is perpendicular to the main plane of the fixation plate,
the screw at the first screw hole of the top-end portion is angled at or about 6.4° relative the line, and
the screw at the first Combi hole is angled at or about 32.45° relative the line.

Aspect 28. The tibial osteotomy below the tibial tuberosity as in any one of aspects 24-26, wherein fixating the cut tibia with a fixation plate includes installing screws into the first, second, and third screw holes of the top-end portion and the first and second screw holes of the bottom-end portion, respectively,
wherein the angle between the screw at the first Combi hole and the screw at the third screw hole of the top-end portion is at or about 20.912°, the angle between the screw at the first Combi hole and the screw at the first screw hole of the top-end portion is at or about 1.345°, the angle between the screw at the first Combi hole and the screw at the second screw hole of the top end-portion is at or about 1.802°.

Although the embodiments above are related to osteotomy of the tibia, it is understood that that fixation plate can also be used in fixating a fractured tibia. Furthermore, it is understood that the embodiments herein can also be applicable to a long bone other than the tibia with or without significant modification to the embodiments discussed above.

We claim:

1. A fixation plate for internal fixation of an osteotomy below the tuberosity of a tibia, comprising an elongated body having a top end and a bottom end opposing the top end along the length direction of the fixation plate,
wherein the elongated body, viewed from the top end to the bottom end, comprises:
a top-end portion comprising a first pinhole, a second pinhole, a third pinhole, a first screw hole, a second screw hole, a third screw hole, and a first Combi hole;
a bottom-end portion comprising a second Combi hole, a first screw hole, a pinhole, and a second screw hole; and
a connection portion connecting the top-end portion to the bottom-end portion,
wherein the first, second, and third screw holes of the top-end portion are arranged in an inverted oblique triangle configuration where the third screw hole of the top-end portion is disposed below the first and second screw holes of the top-end portion,
the first, second, and third pinhole of the top-end portion alternate with the first, second, and third screw hole of the top-end portion,
the first Combi hole is disposed below the first pinhole, the second pinhole, the third pinhole, the first screw hole, the second screw hole, and the third screw hole of the top-end portion,
centers of the first, second, and third pinholes of the top-end portion are disposed outside of a triangle formed by the centers of the first, second, and third screw holes of the top-end portion,
the second Combi hole is disposed above the first screw hole, the pinhole, and the second screw hole of the bottom-end portion, and
the fixation plate has a length in a range of 111.0 to 112.0 mm, the top-end portion has a width in a range of 27.3 mm to 27.7 mm, and the bottom-end portion has a width in a range of 17.5 mm to 17.7 mm.

2. The fixation plate of claim 1, wherein the third screw hole of the top-end portion has an equal distance to the first screw hole and the second screw hole of the top-end portion.

3. The fixation plate of claim 1, wherein centers of the first Combi hole, the second Combi hole, and the first and second screw holes of the bottom-end portion are aligned along with a mid-width line of the bottom-end portion.

4. The fixation plate of claim 1, wherein each of the first and the second Combi holes includes one threaded hole section and one DCP hole section.

5. The fixation plate of claim 1, wherein the first and the second Combi holes are identical to each other.

6. The fixation plate of claim 1, wherein the connection portion is not provided with a through-hole.

7. The fixation plate of claim 1, wherein the pinhole of the bottom end portion is disposed between the first and the second screw holes of the bottom end portion.

8. The fixation plate of claim 1, wherein the top-end portion is laterally offset relative to the bottom-end portion.

9. The fixation plate of claim 1, wherein the top-end portion is bendable or twistable or bent or twisted to fit a three-dimensional contour above a cut of the osteotomy.

10. The fixation plate of claim 1, wherein the bottom-end portion is strip-shaped.

11. The fixation plate of claim 1, wherein the bottom-end portion has a semicircular distal end.

12. The fixation plate of claim 1, wherein the first and second Combi holes each are configured so that screws therein do not go in or through a cut of the osteotomy.

13. The fixation plate of claim 1, wherein at least one of the first and second screw holes of the bottom-end portion is a conical screw hole.

14. The fixation plate of claim 1, wherein the second screw hole of the bottom-end portion is closer to the distal end of the bottom-end portion than the first screw hole of the bottom-end portion, and the second screw hole of the bottom-end portion is a double lead conical thread hole having a pitch of 0.5 mm, a thread thickness of 0.425 mm, and a cone degree of 19.8° to 20.2°.

15. The fixation plate of claim 1, wherein the second screw hole of the bottom-end portion is closer to the distal end of the bottom-end portion than the first screw hole of the bottom-end portion, and the second screw hole of the bottom-end portion has an angle of 59.8° to 60.2° relative to the center of the bottom end.

16. The fixation plate of claim 1, wherein the top-end portion is curled or bent out the plane of the connection portion and the bottom-end portion at an angle in a range of −20° to 20°.

17. A tibial osteotomy below the tibial tuberosity, comprising;

cutting a tibia at a site below the tibial tuberosity to obtain a cut tibia; and fixating the cut tibia with the fixation plate of claim 1.

18. The tibial osteotomy below the tibial tuberosity of claim 17, wherein fixating the cut tibia includes installing screws into the first screw hole of the top-end portion, the second screw hole of the top-end portion second, the third screw hole of the top-end portion, the first Combi hole, the second Combi hole, the first screw hole of the bottom-end portion, and the second screw hole of the bottom-end portion, respectively, wherein the screws at the second Combi hole, the first screw hole, and the second screw hole of the bottom-end portion are parallel to each other, and are angled 7.36° relative to a line that is perpendicular to a main plane of the fixation plate, the screw at the first screw hole of the top-end portion is angled 6.4° relative to the line, and the screw at the first Combi hole is angled 32.45° relative to the line.

19. The tibial osteotomy below the tibial tuberosity of claim 17, wherein fixating the cut tibia with a fixation plate includes installing screws into the first screw hole of the top-end portion, the second screw hole of the top-end portion second, the third screw hole of the top-end portion, the first Combi hole, the second Combi hole, the first screw hole of the bottom-end portion, and the second screw hole of the bottom-end portion, respectively, wherein an angle between the screw at the first Combi hole and the screw at the second screw hole of the top-end portion is 20.912°, an angle between the screw at the first Combi hole and the screw at the first screw hole is 1.345°, an angle between the screw at the first Combi hole and the second screw hole of the top-end portion is 1.802°.

* * * * *